(12) United States Patent
Jan et al.

(10) Patent No.: US 7,985,886 B1
(45) Date of Patent: Jul. 26, 2011

(54) AROMATIC ALKYLATION PROCESS USING UZM-37 ALUMINOSILICATE ZEOLITE

(75) Inventors: Deng-Yang Jan, Elk Grove Village, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/751,449

(22) Filed: Mar. 31, 2010

(51) Int. Cl.
*C07C 2/66* (2006.01)
(52) U.S. Cl. ....................................... 585/467
(58) Field of Classification Search .................. 585/467
See application file for complete search history.

(56) References Cited

U.S. PATENT DOCUMENTS

| | | | |
|---|---|---|---|
| 4,440,871 A * | 4/1984 | Lok et al. ...................... | 502/214 |
| 4,528,171 A | 7/1985 | Casci et al. | |
| 6,892,511 B2 | 5/2005 | Wagner | |
| 7,575,737 B1 | 8/2009 | Miller et al. | |
| 7,578,993 B2 | 8/2009 | Lewis et al. | |

* cited by examiner

*Primary Examiner* — Thuan Dinh Dang
(74) *Attorney, Agent, or Firm* — Maryann Maas

(57) ABSTRACT

A new family of crystalline aluminosilicate zeolites has been synthesized. These zeolites are represented by the empirical formula.

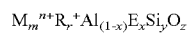

$$M_m{}^{n+}R_r{}^+Al_{(1-x)}E_xSi_yO_z$$

where M represents a combination of potassium and sodium exchangeable cations, R is a singly charged organoammonium cation such as the propyltrimethylammonium cation and E is a framework element such as gallium. These zeolites are similar to MWW but are characterized by unique x-ray diffraction patterns and compositions and have catalytic properties for carrying out alkylation processes.

20 Claims, No Drawings

AROMATIC ALKYLATION PROCESS USING UZM-37 ALUMINOSILICATE ZEOLITE

FIELD OF THE INVENTION

The present invention relates to the use of zeolite UZM-37 in a process for the alkylation of aromatic hydrocarbons, in particular for the production of ethylbenzene or cumene. In the alkylation process, the zeolite UZM-37 may be present in the alkylation catalyst as the sole zeolite component or may be combined with at least one additional zeolite component. The zeolite UZM-37 may be present in the catalyst as unmodified zeolite UZM-37 or as UZM-37 modified zeolite. The UZM-37 containing catalyst may take one of several forms, including for example, a spherical oil-dropped catalyst or an extruded catalyst.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Topological zeolites can be used as catalysts for hydrocarbon conversion reactions, which can take place on outside surfaces as well as on internal surfaces within the pore.

In U.S. Pat. No. 4,528,171 an EU-4 zeolite is described. The template propyltrimethylammonium hydroxide is used in the synthesis of EU-4. However, the silica to alumina ratio of the product EU-4 is higher than 49.1.

In U.S. Pat. No. 6,892,511 another zeolite, UZM-15, is described. The template propyltrimethylammonium hydroxide is used in the synthesis of UZM-15, but only as an additive to another template; and not as the sole template.

In U.S. Pat. No. 7,575,737 another zeolite, UZM-27 is synthesized with a propyltrimethylammonium hydroxide template in conjunction with calcium.

Applicants have successfully prepared a new family of materials designated UZM-37. The topology of the materials is similar to that observed for MWW. The materials are prepared via the use of a simple commercially available structure directing agent, such as propyltrimethylammonium hydroxide, using the Charge Density Mismatch Approach to zeolite synthesis (U.S. Pat. No. 7,578,993). The organoammonium compounds used to make UZM-37 zeolite are non-cyclic or contain cyclic substituents and are generally quite simple. Examples of organoammonium compounds used to make UZM-37 include propyltrimethylammonium (PTMA) and isopropyltrimethylammonium (1-PTMA) cations.

Alkylation of aromatic compounds with a C2 to C4 olefin and transalkylation of polyalkylaromatic compounds are two common reactions for producing monoalkylated aromatic compounds such as cumene and ethylbenzene. Examples of these two reactions that are practiced industrially to produce cumene (isopropylbenzene) are the alkylation of benzene with propylene and the transalkylation of benzene and a diisopropylbenzene (DIPB). The alkylation reaction forms cumene and common byproducts such as DIPBs and triisopropylbenzenes (TIPBs). DIPBs, TIPBs, and some of the higher polyisopropylbenzenes can be readily transalkylated by benzene to produce cumene. Alkylation and transalkylation reactions may be combined in one process unit in a single reaction zone or multiple reaction zones.

The UZM-37 family of materials is effective in carrying out the alkylation of aromatic with alkylating reagents. It is able to provide and maintain high conversion of olefins such as ethylene and propylene, high selectivity to mono-alkylated products such as ethylbenzene and cumene (isopropylbenzene), and high total alkylated selectivity over a range of benzene to olefin molar ratios of interest to commercial operation due to UZM-37's particular pore geometry and framework Si/Al ratio. The UZM-37 zeolite contains significant amounts of Al in the tetrahedral framework, with the mole ratio of Si/Al ranging from about 8 to about 20.

SUMMARY OF THE INVENTION

The present invention relates to a process of aromatic alkylation using a catalyst of the aluminosilicate zeolite designation UZM-37. The process comprises contacting olefinic and alkylatable aromatic hydrocarbons with the UZM-37 zeolite at alkylation conditions to give an alkylated aromatic product.

The UZM-37 aluminosilicate zeolite is a microporous crystalline zeolite having a three-dimensional framework of at least $AlO_2$ and $SiO_2$ tetrahedral units and an empirical composition in the as synthesized and anhydrous basis expressed by an empirical formula of:

$$M_m^{+}R_r^{+}Al_{1-x}E_xSi_yO_z$$

where M represents sodium or a combination of sodium/potassium or lithium/strontium exchangeable cations, "m" is the mole ratio of M to (Al+E) and varies from about 0.05 to about 2, R is a singly charged organoammonium cation propyltrimethylammonium hydroxide, "r" is the mole ratio of R to (Al+E) and has a value of about 0.25 to about 5.0, E is an element selected from the group consisting of gallium, iron, boron and mixtures thereof, "x" is the mole fraction of E and has a value from 0 to about 1.0, "y" is the mole ratio of Si to (Al+E) and varies from greater than 7 to about 20 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A

TABLE A

| 2θ | d (Å) | I/Io % |
|---|---|---|
| 3.22-3.48 | 25.35-27.44 | m |
| 6.62-6.92 | 12.76-13.34 | m |
| 7.12-7.39 | 11.93-12.4 | s-vs |
| 7.92-8.32 | 10.61-11.15 | m |
| 8.64-8.81 | 10.01-10.22 | m |
| 9.71-9.85 | 8.97-9.09 | m |
| 12.75-12.78 | 6.92-6.93 | w |
| 13.39-13.72 | 6.44-6.6 | w |
| 14.34-14.5 | 6.1-6.17 | w |
| 20.13-20.2 | 4.39-4.4 | m |
| 21.56-21.64 | 4.1-4.11 | m |

TABLE A-continued

| 2θ | d (Å) | I/Io % |
|---|---|---|
| 22.14-22.28 | 3.98-4.01 | m |
| 23.09-23.35 | 3.8-3.84 | m |
| 23.95-23.97 | 3.7-3.71 | w-m |
| 24.92-25.19 | 3.53-3.57 | m |
| 25.92-26.21 | 3.39-3.43 | vs |
| 26.7-26.77 | 3.32-26.7 | m |
| 28.99-29.32 | 3.04-3.07 | w-m |
| 31.51-31.64 | 2.82-2.83 | w |
| 33.3-33.69 | 2.65-2.68 | w |
| 37.68-37.94 | 2.36-2.38 | w |
| 46.05-46.29 | 1.95-1.96 | w |
| 48.78-48.94 | 1.85-1.86 | w | and is thermally stable up to a temperature of greater than 600° C. in one embodiment and 700° C. in another embodiment. The BET surface area is less than 420 m²/g.

The process for preparing UZM-37 comprises forming a reaction mixture containing reactive sources of M, R, Al, Si and optionally E and heating the reaction mixture at a temperature of about 150° C. to about 200° C., or about 165° C. to about 185° C., for a time sufficient to form the zeolite, the reaction mixture having a composition expressed in terms of mole ratios of the oxides of:

$$aM_2O:bR_{2/p}O:1-cAl_2O_3:cE_2O_3:dSiO_2:eH_2O$$

where "a" has a value of about 0.05 to about 25, "b" has a value of about 1.5 to about 80, "c" has a value of 0 to about 1.0, "d" has a value of about 8 to about 40, "e" has a value of about 25 to about 4000.

Yet another embodiment of the invention is a catalytic process for alkylation of aromatic hydrocarbons using the above-described zeolite. The process comprises contacting the light olefin and the aromatic hydrocarbon with the zeolite at conversion conditions to give an alkylated aromatic hydrocarbon.

DETAILED DESCRIPTION OF THE INVENTION

Applicants have prepared an aluminosilicate zeolite whose topological structure is similar to MWW as described in *Atlas of Zeolite Framework Types*, which is maintained by the International Zeolite Association Structure Commission at http://topaz.ethz.ch/IZA-SC/StdAtlas.htm, which has been designated UZM-37. As will be shown in detail, UZM-37 is different from MWW in a number of its characteristics. The instant microporous crystalline zeolite (UZM-37) has an empirical composition in the as-synthesized form and on an anhydrous basis expressed by the empirical formula:

$$M_m^+R_r^+Al_{1-x}E_xSi_yO_z$$

where M represents sodium or a combination of sodium/potassium or lithium/strontium exchangeable cations. R is a singly charged organoammonium cation, examples of which include but are not limited to the propyltrimethylammonium cation, iso-propyltrimethyl cation, dimethyldipropylammonium cation (DMDPA⁺), choline [(CH₃)₃N(CH₂)₂OH]⁺, ETMA⁺, DEDMA⁺, trimethylbutylammonium, dimethyldiethanolammonium, methyltripropylammonium, TEA⁺, TPA⁺ and mixtures thereof and "r" is the mole ratio of R to (Al+E) and varies from about 0.25 to about 2.0 while "m" is the mole ratio of M to (Al+E) and varies from about 0.05 to about 3. The ratio of silicon to (Al+E) is represented by "y" which varies from about 8 to about 40. E is an element which is tetrahedrally coordinated, is present in the framework and is selected from the group consisting of gallium, iron and boron. The mole fraction of E is represented by "x" and has a value from 0 to about 1.0, while "z" is the mole ratio of O to (Al+E) and is given by the equation:

$$z=(m·n+r+3+4·y)/2.$$

Where M is only one metal, then the weighted average valence is the valence of that one metal, i.e. +1 or +2. However, when more than one M metal is present, the total amount of:

$$M_m^{n+} = M_{m1}^{(n1)+} + M_{m2}^{(n2)+} + M_{m3}^{(n3)+} + \ldots$$

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

The microporous crystalline zeolite, UZM-37, is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals, potassium and sodium, include the halide salts, nitrate salts, acetate salts, and hydroxides of the respective alkali metals. R is an organoammonium cation selected from the group consisting of propyltrimethylammonium, isopropyltrimethylammonium, dimethyldipropylammonium, choline, ETMA, DEDMA, TEA, TPA, trimethylbutylammonium, dimethyldiethanolammonium and mixtures thereof, and the sources include the hydroxide, chloride, bromide, iodide and fluoride compounds. Specific examples include without limitation propyltrimethylammonium hydroxide, propyltrimethylammonium chloride, propyltrimethylammonium bromide, iso-propyltrimethylammonium hydroxide, iso-propyltrimethylammonium chloride, iso-propyltrimethylammonium bromide, dimethyldipropylammonium hydroxide, ethyltrimethylammonium hydroxide, diethyldimethylammonium hydroxide, tetraethylammonium hydroxide, tetrapropylammonium hydroxide.

The reaction mixture containing reactive sources of the desired components can be described in terms of molar ratios of the oxides by the formula:

$$aM_2O:bR_{2/p}O:1-cAl_2O_3:cE_2O_3:dSiO_2:eH_2O$$

where "a" varies from about 0.05 to about 1.25, "b" varies from about 1.5 to about 80, "c" varies from 0 to 1.0, "d" varies from about 8 to about 40, and "e" varies from about 25 to about 4000. If alkoxides are used, it is preferred to include a distillation or evaporative step to remove the alcohol hydrolysis products. The reaction mixture is now reacted at a temperature of about 150° C. to about 200° C., about 165° C. to about 185° C., or about 170° C. to about 180° C., for a period of about 1 day to about 3 weeks and preferably for a time of about 5 days to about 12 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. It should be pointed out that UZM-37 seeds can optionally be added to the reaction mixture in order to accelerate the formation of the zeolite.

A preferred synthetic approach to make UZM-37 utilizes the charge density mismatch concept, which is disclosed in U.S. Pat. No. 7,578,993 and *Studies in Surface Science and Catalysis*, (2004), Vol. 154A, 364-372. The method disclosed in U.S. Pat. No. 7,578,993 employs quaternary ammonium hydroxides to solubilize aluminosilicate species, while crystallization inducing agents such as alkali and alkaline earth metals and more highly charged organoammonium cations are often introduced in a separate step. Once some UZM-37 seeds have been generated using this approach, the seeds can be used in a single step synthesis of UZM-37, using, for example, a combination of propyltrimethylammonium hydroxide and the alkali cations. The use of commercially available propyltrimethylammonium hydroxide to prepare UZM-37 offers a great economic advantage over previously employed structure directing agents such as hexamethylimine used to prepare aluminosilicates with the MWW topology. Additionally, propyltrimethyl ammonium hydroxide can be employed as the hydroxide or the chloride in concert with other inexpensive organoammonium hydroxides using the charge density mismatch concept to reduce costs even further.

The UZM-37 aluminosilicate zeolite, which is obtained from the above-described process, is characterized by the x-ray diffraction pattern, having at least the d-spacings and relative intensities set forth in Table A below.

TABLE A

| 2θ | d (Å) | I/Io % |
|---|---|---|
| 3.22-3.48 | 25.35-27.44 | m |
| 6.62-6.92 | 12.76-13.34 | m |
| 7.12-7.39 | 11.93-12.4 | s-vs |
| 7.92-8.32 | 10.61-11.15 | m |
| 8.64-8.81 | 10.01-10.22 | m |
| 9.71-9.85 | 8.97-9.09 | m |
| 12.75-12.78 | 6.92-6.93 | w |
| 13.39-13.72 | 6.44-6.6 | w |
| 14.34-14.5 | 6.1-6.17 | w |
| 20.13-20.2 | 4.39-4.4 | m |
| 21.56-21.64 | 4.1-4.11 | m |
| 22.14-22.28 | 3.98-4.01 | m |
| 23.09-23.35 | 3.8-3.84 | m |
| 23.95-23.97 | 3.7-3.71 | w-m |
| 24.92-25.19 | 3.53-3.57 | m |
| 25.92-26.21 | 3.39-3.43 | vs |
| 26.7-26.77 | 3.32-26.7 | m |
| 28.99-29.32 | 3.04-3.07 | w-m |
| 31.51-31.64 | 2.82-2.83 | w |
| 33.3-33.69 | 2.65-2.68 | w |
| 37.68-37.94 | 2.36-2.38 | w |
| 46.05-46.29 | 1.95-1.96 | w |
| 48.78-48.94 | 1.85-1.86 | w |

As will be shown in detail in the examples, the UZM-37 material is thermally stable up to a temperature of at least 600° C. and in another embodiment, up to about 700° C. The characteristic diffraction lines associated with typical calcined UZM-37 samples are shown in Table B.

TABLE B

| 2θ | d (Å) | I/Io % |
|---|---|---|
| 7.28-7.45 | 11.84-12.1 | s-vs |
| 8.04-8.18 | 10.79-10.98 | m |
| 10.02-10.21 | 8.64-8.82 | m |
| 12.91-13.15 | 6.72-6.81 | m |
| 14.52-14.69 | 6.02-6.08 | m-s |
| 19-19.16 | 4.62-4.66 | w |
| 19.79-19.92 | 4.45-4.48 | w-m |
| 20.36-20.53 | 4.32-4.33 | m |
| 22.03-22.15 | 4-4.03 | m |
| 22.8-22.9 | 3.88-3.89 | s-vs |
| 23.82-24.02 | 3.7-3.73 | m |
| 25.24-25.3 | 3.51-3.52 | m |
| 26.2-26.36 | 3.37-3.39 | vs |
| 27.06-27.24 | 3.27-3.29 | m |
| 27.88-27.97 | 3.18-3.19 | m |
| 28.15-28.33 | 3.14-3.16 | m |

As synthesized, the UZM-37 material will contain some of the exchangeable or charge balancing cations in its pores. These exchangeable cations can be exchanged for other cations, or in the case of organic cations, they can be removed by heating under controlled conditions. The UZM-37 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Properties that are modified include porosity, adsorption, Si/Al ratio, acidity, thermal stability, etc.

The UZM-37 compositions which are modified by one or more techniques described in the '975 patent (herein UZM-37HS) are described by the empirical formula on an anhydrous basis of:

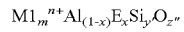

$$M1_m^{n+}Al_{(1-x)}E_xSi_{y'}O_{z''}$$

where M1 is at least one exchangeable cation selected from the group consisting of alkali, alkaline earth metals, rare earth metals, ammonium ion, hydrogen ion and mixtures thereof, "a" is the mole ratio of M1 to (Al+E) and varies from about 0.05 to about 50, "n" is the weighted average valence of M1 and has a value of about +1 to about +3, E is an element selected from the group consisting of gallium, iron, boron, and mixtures thereof, "x" is the mole fraction of E and varies from 0 to 1.0, y' is the mole ratio of Si to (Al+E) and varies from greater than about 4 to virtually pure silica and z' is the mole ratio of O to (Al+E) and has a value determined by the equation:

$$z'=(a \cdot n+3+4 \cdot y')/2$$

By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 4 to 3,000 preferably greater than 10 to about 3,000; 4 to 10,000 preferably greater than 10 to about 10,000 and 4 to 20,000 preferably greater than 10 to about 20,000.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The UZM-37 zeolite as outlined above or a modification thereof, is used as a catalyst or catalyst support in various alkylation reactions of aromatic hydrocarbons. The zeolite preferably is mixed with a binder for convenient formation of catalyst particles in a proportion of about 5 to 100 mass % zeolite and 0 to 95 mass-% binder, with the zeolite preferably comprising from about 10 to 90 mass-% of the composite. The binder should preferably be porous, have a surface area of about 5 to about 800 m²/g, and be relatively refractory to the conditions utilized in the hydrocarbon conversion process. Non-limiting examples of binders are alumina, titania, zirconia, zinc oxide, magnesia, boria, silica-alumina, silica-magnesia, chromia-alumina, alumina-boria, aluminophosphates, silica-zirconia, silica, silica gel, and clays. Preferred binders are amorphous silica and alumina, including gamma-, eta-, and theta-alumina, with gamma- and eta-alumina being especially preferred.

The zeolite with or without a binder can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50 to about 200° C. and subjected to a calcination procedure at a temperature of about 450 to about 700° C. for a period of about 1 to about 20 hours. This treatment effects conversion of the hydrogel to the corresponding alumina matrix.

The interaction of the feed molecules with the catalyst is of great importance in catalysis. This interaction may be characterized by the contact time. Contact time is calculated by dividing the catalyst volume by the feed flow rate. Lower contact times indicate less interaction of the feed with the catalyst, while higher contact times indicate high interaction of the feed with the catalyst. Selectivity to specific products may be altered by altering the contact time. For reactions such as alkylation of aromatic hydrocarbons, where a feedstock containing an alkylatable hydrocarbon and a stream comprising at least one olefin are both passed over the catalyst, the contact time is calculated using the olefin or the combined feed rate.

The alkylation and preferably the monoalkylation of aromatic compounds involves reacting an alkylatable aromatic compound with an alkylating reagent such as olefin using the above described zeolitic catalyst. The olefins which can be used in the instant process are any of those which contain from 2 up to about 6 carbon atoms. These olefins may be branched or linear olefins and either terminal or internal olefins. Preferred olefins are ethylene, propylene, butenes and amylenes.

The alkylatable aromatic compounds may be selected from the group consisting of benzene, naphthalene, anthracene, phenanthrene, and substituted derivatives thereof, with benzene and its derivatives being the most preferred aromatic compound. By alkylatable is meant that the aromatic compound can be alkylated by an olefinic compound. The alkylatable aromatic compounds may have one or more of the substituents selected from the group consisting of alkyl groups (having from 1 to about 20 carbon atoms), hydroxyl groups, and alkoxy groups whose alkyl group also contains from 1 up to 20 carbon atoms. Where the substituent is an alkyl or alkoxy group, a phenyl group can also be substituted on the alkyl chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, phenol, cresol, anisole, ethoxy-, propoxy-, butoxy-, pentoxy-, hexoxybenzene, etc.

Reactions involving the alkylation of aromatic hydrocarbons are processes well known in the art and include the production of ethylbenzene and cumene. Specific reaction conditions and the types of feeds which can be used in these processes are set forth in: U.S. Pat. No. 7,498,472, U.S. Pat. No. 7,525,003, U.S. Pat. No. 7,525,004, U.S. Pat. No. 7,420,098, U.S. Pat. No. 7,525,005, U.S. Pat. No. 7,525,006 which are all hereby incorporated by reference in their entirety. As can be seen in the final example, using UZM-37 as the catalyst or as a component of the catalyst for aromatic alkylation results in high total alkylation of the aromatic hydrocarbons, as compared to an upper limit of equilibrium. With the product slate containing very high amounts of the desired product, little amounts of undesired side products are generated. Further, the process is successful with low benzene to olefin ratios which helps to reduce the cost and utilities of the process.

The structure of the UZM-37 zeolite used herein was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100×I/I$_o$, the above designations are defined as:

w=0-15; m=15-60: s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In the following examples, the BET surface area and micropore volumes of the materials were determined using UOP Method 964-98.

In order to more fully illustrate the invention, the following examples are set forth. It is to be understood that the examples are only by way of illustration and are not intended as an undue limitation on the broad scope of the invention as set forth in the appended claims.

EXAMPLE 1

An aluminosilicate solution was prepared by first mixing 39.81 aluminum hydroxide (28.22% Al) and 1371.36 g propyltrimethylammonium hydroxide, 21.9% solution, with vigorous stirring. After thorough mixing, 952.5 g of Ludox™ AS-40 (39.8% SiO$_2$) was added. The reaction mixture was homogenized for an additional hour with a high speed mechanical stirrer and placed in an oven at 100° C. overnight. Analysis showed the resulting aluminosilicate solution contained 7.58 wt. % Si and 0.49 wt. % Al yielding a Si/Al ratio of 14.86.

To a 1000 g portion of the aluminosilicate solution prepared in Example 1, an aqueous NaCl solution containing 21.16 g of NaCl (98%) dissolved in 100.0 g distilled water was added with vigorous stirring and the reaction mixture was homogenized for an additional 30 minutes. A 1067 g portion of the reaction mixture was transferred to a 2000 ml Parr stainless steel autoclave which was heated to 175° C. and maintained at that temperature for 168 hrs. The solid product was recovered by filtration, washed with de-ionized water, and dried at 100° C.

The product was identified as UZM-37 by xrd. Representative diffraction lines observed for the product are shown in Table 1. The product composition was determined by elemental analysis to consist of the following mole ratios: Si/Al=13.02, Na/Al=0.57, N/Al=1.32, C/N=5.94. A portion of the material was calcined by ramping to 600° C. in air for 2 hrs followed by a 2 hr dwell in air. The BET surface area was found to be 378 m2/g and the micropore volume was 0.16 cc/g.

TABLE 1

| 2θ | d(Å) | I/I$_0$ % |
|---|---|---|
| 3.37 | 26.12 | m |
| 6.77 | 13.03 | m |
| 7.26 | 12.16 | s |
| 8.16 | 10.82 | m |
| 8.64 | 10.22 | m |
| 9.71 | 9.09 | m |
| 12.75 | 6.93 | w |
| 14.44 | 6.12 | w |
| 20.15 | 4.4 | m |
| 21.64 | 4.1 | m |
| 22.14 | 4.01 | m |

TABLE 1-continued

| 2θ | d(Å) | I/I$_0$ % |
|---|---|---|
| 23.3 | 3.81 | m |
| 23.95 | 3.71 | m |
| 25.08 | 3.54 | m |
| 26.07 | 3.41 | vs |
| 26.72 | 3.33 | m |
| 29.26 | 3.04 | w |
| 31.62 | 2.82 | w |
| 33.69 | 2.65 | w |
| 37.88 | 2.37 | w |
| 46.15 | 1.96 | w |
| 48.83 | 1.86 | w |
| 51.3 | 1.77 | w |

Scanning Electron Microscopy (SEM) revealed crystals of plate shaped morphology, approximately 400 nm by 600 nm in size. This sample was calcined at 600° C. for 2 hrs under air. Representative diffraction lines observed for the product are shown in Table 2.

TABLE 2

| 2θ | d(Å) | I/I$_0$ % |
|---|---|---|
| 4.06 | 21.74 | w |
| 7.28 | 12.13 | s |
| 8.12 | 10.87 | m |
| 10.04 | 8.8 | m |
| 12.91 | 6.84 | m |
| 14.52 | 6.09 | m |
| 16.03 | 5.52 | m |
| 19.16 | 4.62 | w |
| 20.36 | 4.35 | m |
| 22.06 | 4.02 | m |
| 22.8 | 3.89 | s |
| 24.02 | 3.7 | m |
| 25.3 | 3.51 | m |
| 26.2 | 3.39 | vs |
| 27.09 | 3.28 | m |
| 27.97 | 3.18 | w |
| 46.54 | 1.94 | w |

EXAMPLE 2

To a 1000 g portion of the aluminosilicate solution prepared in Example 1, an aqueous NaCl solution containing 15.87 g of NaCl (98%) dissolved in 100.0 g distilled water was added with vigorous stirring and the reaction mixture was homogenized for an additional 30 minutes. A 1050 g portion of the reaction mixture was transferred to a 2000 ml Parr stainless steel autoclave which was heated to 175° C. and maintained at that temperature for 168 hrs. The solid product was recovered by filtration, washed with de-ionized water, and dried at 100° C.

The product was identified as UZM-37 by xrd. Representative diffraction lines observed for the product are shown in Table 3. The product composition was determined by elemental analysis to consist of the following mole ratios: Si/Al=13.21, Na/A=0.45, N/Al=1.37, C/N=5.90. A portion of the material was calcined by ramping to 600° C. in air for 2 hrs followed by a 2 hr dwell in air. The BET surface area was found to be 401 m$^2$/g and the micropore volume was 0.164 cc/g. Scanning Electron Microscopy (SEM) revealed crystals of plate shaped morphology, approximately 500 nm by 600 nm in size.

TABLE 3

| 2θ | d(Å) | I/I₀% |
|---|---|---|
| 3.31 | 26.59 | m |
| 6.77 | 13.02 | m |
| 7.24 | 12.19 | vs |
| 8.12 | 10.87 | m |
| 8.81 | 10.01 | m |
| 9.28 | 9.52 | m |
| 12.78 | 6.92 | w |
| 13.58 | 6.51 | w |
| 15.84 | 5.58 | w |
| 20.19 | 4.39 | m |
| 21.63 | 4.1 | m |
| 22.18 | 4 | m |
| 22.76 | 3.9 | m |
| 23.35 | 3.8 | m |
| 23.53 | 3.77 | m |
| 23.77 | 3.73 | m |
| 23.97 | 3.7 | w |
| 25.11 | 3.54 | m |
| 26.07 | 3.41 | vs |
| 26.76 | 3.32 | m |
| 28.99 | 3.07 | w |
| 31.64 | 2.82 | w |
| 33.69 | 2.65 | w |
| 37.82 | 2.37 | w |
| 46.29 | 1.95 | w |
| 48.94 | 1.85 | w |
| 51.62 | 1.76 | w |

EXAMPLE 3

An aluminosilicate solution was prepared by first mixing 13.27 g aluminum hydroxide (28.22% Al) and 457.12 g propyltrimethylammonium hydroxide, 21.9% solution, with vigorous stirring. After thorough mixing, 317.50 g of Ludox™ AS-40 (39.8% SiO₂) was added. The reaction mixture was homogenized for an additional hour with a high speed mechanical stirrer and placed in an oven at 100° C. overnight. Analysis showed the resulting aluminosilicate solution contained 7.71 wt. % Si and 0.49 wt. % Al yielding a Si/Al ratio of 15.15.

A 790 g portion of the aluminosilicate solution was placed in a container and an aqueous NaCl solution containing 16.71 g of NaCl (98%) dissolved in 80.0 g distilled water was added with vigorous stirring and the reaction mixture was homogenized for an additional 30 minutes. A 850 g portion of the reaction mixture was transferred to a 2000 ml Parr stainless steel autoclave which was heated to 175° C. and maintained at that temperature for 144 hrs. The solid product was recovered by filtration, washed with de-ionized water, and dried at 100° C.

The product was identified as UZM-37 by xrd. Representative diffraction lines observed for the product are shown in Table 4. The product composition was determined by elemental analysis to consist of the following mole ratios: Si/Al=12.86, Na/A=0.55, N/Al=1.40, C/N=5.7. A portion of the material was calcined by ramping to 600° C. in air for 2 hrs followed by a 2 hr dwell in air. The BET surface area was found to be 342 m²/g and the micropore volume was 0.14 cc/g.

TABLE 4

| 2θ | d(Å) | I/I₀% |
|---|---|---|
| 3.22 | 27.44 | m |
| 6.62 | 13.34 | m |
| 7.12 | 12.40 | s |
| 7.92 | 11.15 | m |
| 8.79 | 10.04 | m |
| 9.85 | 8.97 | m |
| 13.39 | 6.60 | w |
| 14.34 | 6.17 | w |
| 20.13 | 4.40 | m |
| 21.56 | 4.11 | m |
| 22.18 | 4.00 | m |
| 23.25 | 3.82 | m |
| 24.92 | 3.57 | m |
| 25.92 | 3.43 | vs |
| 26.7 | 3.33 | m |
| 29.01 | 3.07 | m |
| 31.51 | 2.83 | w |
| 33.65 | 2.68 | w |
| 37.68 | 2.38 | w |
| 46.05 | 1.96 | w |
| 48.78 | 1.86 | w |

EXAMPLE 4

An aluminosilicate solution was prepared by first mixing 13.27 g aluminum hydroxide (28.22% Al) and 457.12 g propyltrimethylammonium hydroxide, 21.9% solution, with vigorous stirring. After thorough mixing, 317.50 g of Ludox™ AS-40 (39.8% SiO₂) was added. The reaction mixture was homogenized for an additional hour with a high speed mechanical stirrer and placed in an oven at 100° C. overnight. Analysis showed the resulting aluminosilicate solution contained 7.47 wt. % Si and 0.47 wt. % Al yielding a Si/Al ratio of 15.3.

A 55 g portion of the aluminosilicate solution was placed in a container and an aqueous NaOH and KOH solution containing 0.19 g of NaOH (98%) and 0.26 g KOH dissolved in 10.0 g distilled water was added with vigorous stirring and the reaction mixture was homogenized for an additional 30 minutes. A 20 g portion of the above reaction mixture was transferred to a 45 ml Parr stainless steel autoclave which was heated to 175° C. and maintained at that temperature for 240 hrs. The solid product was recovered by filtration, washed with de-ionized water, and dried at 100° C.

The product was identified as UZM-37 by xrd. Representative diffraction lines observed for the product are shown in Table 5. The product composition was determined by elemental analysis to consist of the following mole ratios: Si/Al=12.68, Na/A=0.10, K/Al=0.07, N/Al=1.13, C/N=6.0. A portion of the material was calcined by ramping to 600° C. in air for 2 hrs followed by a 2 hr dwell in air. The BET surface area was found to be 352 m²/g and the micropore volume was 0.14 cc/g.

TABLE 5

| 2θ | d(Å) | I/I₀% |
|---|---|---|
| 3.48 | 25.35 | m |
| 6.92 | 12.76 | m |
| 7.39 | 11.93 | s |
| 8.32 | 10.61 | m |
| 9.83 | 8.98 | m |
| 13.72 | 6.44 | w |
| 14.50 | 6.10 | w |
| 20.20 | 4.39 | m |
| 22.28 | 3.98 | m |
| 23.09 | 3.84 | m |
| 23.95 | 3.71 | m |
| 25.19 | 3.53 | m |
| 26.21 | 3.39 | vs |
| 26.77 | 3.32 | m |

TABLE 5-continued

| 2θ | d(Å) | I/I₀ % |
|---|---|---|
| 29.32 | 3.04 | w |
| 33.3 | 2.68 | w |
| 37.94 | 2.36 | w |

EXAMPLE 5

UZM-37 synthesized as per Example 1 was formulated into a catalyst containing 70% zeolite and 30% alumina. In the catalyst preparation Capatal B alumina was first peptized with nitric acid using 0.17 gram of HNO₃ per gram of Capatal B alumina. The peptized alumina was then added to a muller containing zeolite. Additional water was added to the muller, while mixing, until dough with a proper texture for extrusion was formed. The dough was the extruded to form 1/16" diameter cylinders, which were dried at 100° C. overnight and then sized to a length to diameter ratio of approximately 3. The dry extrudate was calcined in a box oven with a flowing air at 600° C. for 2 hours to remove the template. The calcined support was then exchanged using 10 wt-% NH₄NO₃ solution at 70° C. for one hour. This was followed by H₂O wash using 10 grams of water per gram of zeolite. The NH₄NO₃ exchange and water wash was repeated two more times. The extrudate was then dried at 120° C. for 4 hours and then activated at 550° C. BET surface area of the finished catalyst was measured at 328 m²/gram.

The experiment was conducted in a fixed bed reactor equipped with on-line GC under the conditions of 3447 kPa gauge (500 psig) pressure, 115° C. inlet temperatures, benzene to olefin molar ratios between 1.9 and 4.0, and olefin WHSV of about 1.0 hr⁻¹. Part of product effluent was recycled (effluent recycle to fresh feed ration is 7.4 wt./wt.) to mitigate the heat of reaction. The performance is summarized Table 6. It is clear that the UZM-37 containing catalyst gives very high total alkylated selectivity over a range of benzene to olefin ratios and the mono-alkylated selectivity is very close to equilibrium, while the olefin conversions are complete.

TABLE 6

| B/P molar ratios | 2.99 | 2.4 | 2 |
|---|---|---|---|
| GC wt % | | | |
| Benzene wt % | 58.8 | 52.0 | 44.6 |
| cumene wt % | 36.3 | 40.9 | 44.6 |
| DIPB wt % | 4.5 | 6.5 | 9.7 |
| TIPB wt % | 0.2 | 0.4 | 0.8 |
| Activity in End of Active Zone as % bed | 40 | 40 | 40 |
| cumene/(cumene + DIPB + TIPB) mol-% | 91.4 | 89 | 85.5 |
| total alkylated selectivity | 99.81 | 99.8 | 99.76 |

The invention claimed is:

1. A process for alkylating aromatic hydrocarbons comprising contacting a hydrocarbon feedstock comprising at least one alkylatable aromatic and a stream comprising at least one olefin having from 2 to about 6 carbon atoms with a catalyst at alkylation conditions and producing an alkylated aromatic product wherein the catalyst comprises a UZM-37 microporous crystalline zeolite having a three-dimensional framework of at least $AlO_2$ and $SiO_2$ tetrahedral units and an empirical composition in the as synthesized and anhydrous basis expressed by an empirical formula of:

$$M_m{}^+R_rAl_{1-x}E_xSi_yO_z$$

where M represents sodium or a combination of potassium and sodium exchangeable cations, "m" is the mole ratio of M to (Al+E) and varies from about 0.05 to about 2, R is a singly charged propyltrimethylammonium cation, "r" is the mole ratio of R to (Al+E) and has a value of about 0.25 to about 3.0, E is an element selected from the group consisting of gallium, iron, boron and mixtures thereof, "x" is the mole fraction of E and has a value from 0 to about 1.0, "y" is the mole ratio of Si to (Al+E) and varies from greater than 8 to about 40 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A:

TABLE A

| 2θ | d (Å) | I/Io % |
|---|---|---|
| 3.22-3.48 | 25.35-27.44 | m |
| 6.62-6.92 | 12.76-13.34 | m |
| 7.12-7.39 | 11.93-12.4 | s-vs |
| 7.92-8.32 | 10.61-11.15 | m |
| 8.64-8.81 | 10.01-10.22 | m |
| 9.71-9.85 | 8.97-9.09 | m |
| 12.75-12.78 | 6.92-6.93 | w |
| 13.39-13.72 | 6.44-6.6 | w |
| 14.34-14.5 | 6.1-6.17 | w |
| 20.13-20.2 | 4.39-4.4 | m |
| 21.56-21.64 | 4.1-4.11 | m |
| 22.14-22.28 | 3.98-4.01 | m |
| 23.09-23.35 | 3.8-3.84 | m |
| 23.95-23.97 | 3.7-3.71 | w-m |
| 24.92-25.19 | 3.53-3.57 | m |
| 25.92-26.21 | 3.39-3.43 | vs |
| 26.7-26.77 | 3.32-26.7 | m |
| 28.99-29.32 | 3.04-3.07 | w-m |
| 31.51-31.64 | 2.82-2.83 | w |
| 33.3-33.69 | 2.65-2.68 | w |
| 37.68-37.94 | 2.36-2.38 | w |
| 46.05-46.29 | 1.95-1.96 | w |
| 48.78-48.94 | 1.85-1.86 | w | is thermally stable up to a temperature of at least 600° C. and has a BET surface area of less than about 420 m²/g.

2. The process of claim 1 wherein the micropore volume of the zeolite is from about 0.12 cc/g to about 0.18 cc/g.

3. The process of claim 1 where the alkylation conditions include a temperature of from 50° C. to 400° C., a pressure of from about 0 to 6895 kPag (about 0 to 1000 psig), an alkylatable aromatic to olefin mole ratio of from 10 to 0.1 and a contact time of from about 0.1 seconds to about 1 hour.

4. The process of claim 3 wherein the UZM-37 zeolite is mixed with a binder in a proportion of about 5 to 100 mass-% zeolite and 0 to 95 mass-% binder.

5. The process of claim 4 wherein the UZM-37 zeolite is mixed with a binder in a proportion of about 10 to 95 mass-% zeolite with the balance, 5 to 90 mass-%, being binder.

6. The process of claim 1 where the alkylatable aromatic of the feedstock comprises an unsubstituted or monosubstituted benzene.

7. The process of claim 1 where the olefin containing stream contains greater than 20 mol % ethylene and the alkylatable aromatic stream contains greater than 10 mol % benzene or monosubstituted benzene.

8. The process of claim 1 where the olefin containing stream contains greater than 50 mol % propylene and the alkylatable aromatic stream contains greater than 10 mol % benzene or monosubstituted benzene.

9. The process of claim 7 where the alkylatable aromatic is benzene and the olefin containing stream is propylene.

10. The process of claim 9 where the alkylation conditions include a temperature of from 80° C. to 300° C., a pressure of from about 1379 to 5515 kPag (about 200 to 800 psig), an benzene:olefin mole ratio of from about 6 to about 0.3 and a contact time of from about 0.1 seconds to about 1 hour.

11. The process of claim 1 where the selectivity to monoalkylated products is greater than about 50 mol %.

12. The process of claim 1 where "x" is zero.

13. An alkylation process comprising contacting a feedstock comprising unsubstituted or monosubstituted benzene and an olefin stream comprising ethylene with a catalyst at alkylation conditions and producing an alkylated aromatic product wherein the catalyst comprises a UZM-37 microporous crystalline zeolite, wherein the UZM-37 has a three-dimensional framework of at least $AlO_2$ and $SiO_2$ tetrahedral units and an empirical composition in the as synthesized and anhydrous basis expressed by an empirical formula of:

$$M_m^{+}R_rAl_{1-x}E_xSi_yO_z$$

where M represents a combination of potassium and sodium exchangeable cations, "m" is the mole ratio of M to (Al+E) and varies from about 0.05 to about 2, R is a singly charged propyltrimethylammonium cation, "r" is the mole ratio of R to (Al+E) and has a value of about 0.25 to about 3.0, E is an element selected from the group consisting of gallium, iron, boron and mixtures thereof, "x" is the mole fraction of E and has a value from 0 to about 1.0, "y" is the mole ratio of Si to (Al+E) and varies from greater than 8 to about 40 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A

TABLE A

| 2θ | d (Å) | I/Io % |
|---|---|---|
| 3.22-3.48 | 25.35-27.44 | m |
| 6.62-6.92 | 12.76-13.34 | m |
| 7.12-7.39 | 11.93-12.4 | s-vs |
| 7.92-8.32 | 10.61-11.15 | m |
| 8.64-8.81 | 10.01-10.22 | m |
| 9.71-9.85 | 8.97-9.09 | m |
| 12.75-12.78 | 6.92-6.93 | w |
| 13.39-13.72 | 6.44-6.6 | w |
| 14.34-14.5 | 6.1-6.17 | w |
| 20.13-20.2 | 4.39-4.4 | m |
| 21.56-21.64 | 4.1-4.11 | m |
| 22.14-22.28 | 3.98-4.01 | m |
| 23.09-23.35 | 3.8-3.84 | m |
| 23.95-23.97 | 3.7-3.71 | w-m |
| 24.92-25.19 | 3.53-3.57 | m |
| 25.92-26.21 | 3.39-3.43 | vs |
| 26.7-26.77 | 3.32-26.7 | m |
| 28.99-29.32 | 3.04-3.07 | w-m |
| 31.51-31.64 | 2.82-2.83 | w |
| 33.3-33.69 | 2.65-2.68 | w |
| 37.68-37.94 | 2.36-2.38 | w |
| 46.05-46.29 | 1.95-1.96 | w |
| 48.78-48.94 | 1.85-1.86 | w | and is thermally stable up to a temperature of at least 600° C. and has a BET surface area of less than about 420 m²/g.

14. The process of claim 13 wherein the alkylation conditions include a temperature of from 50° C. to 400° C., a pressure of from about 1379 to 6895 kPag (about 200 to 1000 psig), an aromatic:olefin mole ratio of from about 10 to about 0.3 and a contact time of from about 0.1 seconds to about 1 hour.

15. The process of claim 13 wherein the UZM-37 zeolite is mixed with a binder in a proportion of about 10 to 90 mass % zeolite and about 10 to 90 mass-% binder.

16. The process of claim 13 where the aromatic feedstock is benzene and the selectivity to ethylbenzene is greater than about 50 mol %.

17. An alkylation process comprising contacting a feedstock comprising unsubstituted or monosubstituted benzene and an olefin stream comprising propylene with a catalyst at alkylation conditions and producing an alkylated aromatic product wherein the catalyst comprises a UZM-37 microporous crystalline zeolite, wherein the UZM-37 has a three-dimensional framework of at least $AlO_2$ and $SiO_2$ tetrahedral units and an empirical composition in the as synthesized and anhydrous basis expressed by an empirical formula of:

$$M_m^{+}R_rAl_{1-x}E_xSi_yO_z$$

where M represents sodium or a combination of potassium and sodium exchangeable cations, "m" is the mole ratio of M to (Al+E) and varies from about 0.05 to about 2, R is a singly charged propyltrimethylammonium cation, "r" is the mole ratio of R to (Al+E) and has a value of about 0.25 to about 3.0, E is an element selected from the group consisting of gallium, iron, boron and mixtures thereof, "x" is the mole fraction of E and has a value from 0 to about 1.0, "y" is the mole ratio of Si to (Al+E) and varies from greater than 8 to about 40 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A:

TABLE A

| 2θ | d (Å) | I/Io % |
|---|---|---|
| 3.22-3.48 | 25.35-27.44 | m |
| 6.62-6.92 | 12.76-13.34 | m |
| 7.12-7.39 | 11.93-12.4 | s-vs |
| 7.92-8.32 | 10.61-11.15 | m |
| 8.64-8.81 | 10.01-10.22 | m |
| 9.71-9.85 | 8.97-9.09 | m |
| 12.75-12.78 | 6.92-6.93 | w |
| 13.39-13.72 | 6.44-6.6 | w |
| 14.34-14.5 | 6.1-6.17 | w |
| 20.13-20.2 | 4.39-4.4 | m |
| 21.56-21.64 | 4.1-4.11 | m |
| 22.14-22.28 | 3.98-4.01 | m |
| 23.09-23.35 | 3.8-3.84 | m |
| 23.95-23.97 | 3.7-3.71 | w-m |
| 24.92-25.19 | 3.53-3.57 | m |
| 25.92-26.21 | 3.39-3.43 | vs |
| 26.7-26.77 | 3.32-26.7 | m |
| 28.99-29.32 | 3.04-3.07 | w-m |
| 31.51-31.64 | 2.82-2.83 | w |
| 33.3-33.69 | 2.65-2.68 | w |
| 37.68-37.94 | 2.36-2.38 | w |
| 46.05-46.29 | 1.95-1.96 | w |
| 48.78-48.94 | 1.85-1.86 | w | is thermally stable up to a temperature of at least 600° C. and has a BET surface area of less than about 420 m²/g.

18. The process of claim 17 where the alkylation conditions include a temperature of from 50° C. to 300° C., a pressure of from about 1379 to 5515 kPag (about 200 to 800 psig), an aromatic:olefin mole ratio of from about 10 to about 0.3 and a contact time of from about 0.1 seconds to about 1 hour.

19. The process of claim 17 wherein the UZM-37 zeolite is mixed with a binder in a proportion of about 10 to 90 mass % zeolite and about 10 to 90 mass-% binder.

20. The process of claim 17 wherein the aromatic feedstock is benzene and the selectivity to cumene is greater than 50 mol-%.

* * * * *